(12) United States Patent
Kitamura et al.

(10) Patent No.: US 10,830,771 B2
(45) Date of Patent: Nov. 10, 2020

(54) PIVKA-II ASSAY METHOD AND METHOD FOR MANUFACTURING REAGENT OR KIT FOR PIVKA-II IMMUNOASSAY

(71) Applicants: FUJIREBIO INC., Tokyo (JP);
SEKISUI MEDICAL CO., LTD., Tokyo (JP)

(72) Inventors: Yoshiyuki Kitamura, Tokyo (JP);
Katsumi Aoyagi, Tokyo (JP)

(73) Assignees: FUJIREBIO INC., Tokyo (JP);
SEKISUI MEDICAL CO., LTD., Tokyo (JP)

( * ) Notice: Subject to any disclaimer, the term of this patent is extended or adjusted under 35 U.S.C. 154(b) by 215 days.

(21) Appl. No.: 15/766,239

(22) PCT Filed: Oct. 6, 2016

(86) PCT No.: PCT/JP2016/079801
§ 371 (c)(1),
(2) Date: Apr. 5, 2018

(87) PCT Pub. No.: WO2017/061546
PCT Pub. Date: Apr. 13, 2017

(65) Prior Publication Data
US 2018/0284119 A1    Oct. 4, 2018

(30) Foreign Application Priority Data

Oct. 7, 2015  (JP) .................................. 2015-199319

(51) Int. Cl.
| | | |
|---|---|---|
| *G01N 33/573* | (2006.01) | |
| *G01N 33/53* | (2006.01) | |
| *C07K 16/36* | (2006.01) | |
| *C07K 16/40* | (2006.01) | |
| *C12N 15/02* | (2006.01) | |

(52) U.S. Cl.
CPC ........... *G01N 33/573* (2013.01); *C07K 16/36* (2013.01); *C07K 16/40* (2013.01); *C12N 15/02* (2013.01); *G01N 33/53* (2013.01); *G01N 33/5306* (2013.01); *G01N 2333/96433* (2013.01)

(58) Field of Classification Search
CPC .. G01N 33/573; G01N 33/53; G01N 33/5306; C07K 16/36; C07K 16/40; C12N 15/02
See application file for complete search history.

(56) References Cited

U.S. PATENT DOCUMENTS

| | | | | |
|---|---|---|---|---|
| 4,780,410 | A * | 10/1988 | Matsuda | G01N 33/86 435/7.4 |
| 5,516,640 | A * | 5/1996 | Watanabe | G01N 33/82 435/7.4 |
| 6,569,634 | B1 | 5/2003 | Hoshino et al. | |
| 6,893,831 | B1 * | 5/2005 | Kanashima | G01N 33/57438 435/13 |
| 2005/0031663 | A1 | 2/2005 | Larsson et al. | |
| 2012/0020972 | A1 | 1/2012 | Yoshimura et al. | |
| 2015/0219638 | A1 | 8/2015 | Yamaguchi et al. | |

FOREIGN PATENT DOCUMENTS

| | | |
|---|---|---|
| EP | 2884277 A1 | 6/2015 |
| JP | 60-60557 A | 4/1985 |
| JP | 5-249108 A | 9/1993 |
| JP | 9-43237 A | 2/1997 |
| JP | 10-197532 A | 7/1998 |
| JP | 2000-146981 A | 5/2000 |
| JP | 2013-541936 A | 11/2013 |
| JP | 2014-35278 A | 2/2014 |

OTHER PUBLICATIONS

International Search Report issued in PCT/JP2016/079801 (PCT/ISA/210), dated Dec. 6, 2016.
Written Opinion of the International Searching Authority issued in PCT/JP2016/079801 (PCT/ISA/237), dated Dec. 6, 2016.
Extended European Search Report, dated Mar. 14, 2019, for European Application No. 16853698.5.
Kinukawa et al., "Epitope characterization of an anti-PIVKA-II antibody and evaluation of a fully automated chemiluminescent immunoassay for PIVKA-II," Elsevier, Clinical Biochemistry, vol. 48, No. 16-17, Aug. 19, 2015, XP055430235, pp. 1120-1125.

* cited by examiner

*Primary Examiner* — Gailene Gabel
(74) *Attorney, Agent, or Firm* — Birch, Stewart, Kolasch & Birch, LLP

(57) ABSTRACT

Disclosed is a means of enabling the construction of a more accurate PIVKA-II immunoassay system using monoclonal antibodies against human prothrombin. The PIVKA-II assay method according to the present invention comprises measuring PIVKA-II in a sample by an immunoassay using an anti-PIVKA-II antibody or an antigen-binding fragment thereof which specifically binds to PIVKA-II and a mixture of a first anti-prothrombin antibody or an antigen-binding fragment thereof which recognizes hydrophilic PIVKA-II molecules and a second anti-prothrombin antibody or an antigen-binding fragment thereof which recognizes hydrophobic PIVKA-II molecules.

8 Claims, 3 Drawing Sheets
Specification includes a Sequence Listing.

PIVKA-II ASSAY METHOD AND METHOD FOR MANUFACTURING REAGENT OR KIT FOR PIVKA-II IMMUNOASSAY

TECHNICAL FIELD

The present invention relates to a PIVKA-II assay method and a method for production of a PIVKA-II assay reagent or kit, which enables full detection of a group of PIVKA-II molecules contained in a sample.

BACKGROUND ART

PIVKA-II (Protein induced by vitamin K absence-II) is a glycoprotein having a structure similar to prothrombin, which is involved in blood coagulation. Prothrombin is a protein with 579 residues, and contains γ-carboxyglutamic acid (Gla) residues generated by γ-carboxylation of 10 glutamic acid (Glu) residues in the vicinity of the N-terminus. The N-terminal region is referred to as the Glu-Gla region. It is known that, during production of prothrombin in the body, incomplete γ-carboxylation may occur due to lack of vitamin K, hepatic insufficiency, administration of a vitamin K antagonist, hepatocellular damage, or the like, and the glycoproteins in which all or part of the 10 residues are Glu residues may be found in blood. These proteins are collectively referred to as PIVKA-II, also called abnormal prothrombin. Recently, it was reported that PIVKA-II was detected at a high concentration in plasma from patients with hepatocellular carcinoma, and it has been used as a marker for diagnosis and monitoring of hepatocellular carcinoma. Prothrombin and PIVKA-II are not different in structure except for the Glu-Gla region, and both of the proteins have two kringle domains (prothrombin fragment 1 (F1) region and prothrombin fragment 2 (F2) region) in the middle region and a thrombin region in the C-terminal region.

As a method of specifically detecting PIVKA-II in a sample, an immunoassay using both a monoclonal antibody that specifically recognizes PIVKA-II and a polyclonal antibody against prothrombin, one of which is used as an immobilized antibody and the other of which is used as a labeled antibody, has been reported (Patent Document 1). However, polyclonal antibodies may vary in their specificity or affinity for prothrombin from lot to lot. To circumvent the problem, multiple lots of polyclonal antibodies should be evaluated for the specificity and affinity; however, monoclonal antibody is more desirable than polyclonal antibody to secure a higher level of specificity.

It is also known that, in the measurement of PIVKA-II by ELISA using, as an immobilized antibody, a monoclonal antibody that specifically recognizes PIVKA-II and a polyclonal antibody against prothrombin as a secondary antibody, thrombin-reactive antibodies contained in the secondary antibody give adverse effects on the assay system intended for serum samples, and results in unstable measured values (Patent Document 2). It is reported in Patent Document 2 that, to address this problem, an antibody that does not react with human thrombin but specifically reacts with human prothrombin is used as a secondary antibody, which enables stable measurement of PIVKA-II level in serum samples. However, even this method has the same problem as that in Patent Document 1 because a polyclonal antibody is used in the method. Furthermore, in the method of Patent Document 2, a complicated antibody purification process is required to remove antibodies against thrombin from a pool of polyclonal antibodies against human prothrombin, in which antibodies that react with prothrombin are obtained using a human prothrombin-affinity column, then dialyzed, and further treated with a human thrombin-affinity column to obtain antibodies that do not react with thrombin, which antibodies are further dialyzed thereafter.

As another example of the technique of measuring PIVKA-II by ELISA, a technique of measuring PIVKA-II by using an anti-PIVKA-II monoclonal antibody as an immobilized antibody and a mixture of anti-PIVKA-II F1 and F2 monoclonal antibodies as a labeled antibody has been reported (Patent Document 3). According to this technique, the correlation between serum and plasma levels can be improved in paired serum and plasma samples that are collected almost at the same time from an identical patient. However, it is not the subject of Patent Document 3 whether the accuracy of the PIVKA-II detection is increased or not.

Furthermore, the Glu-Gla region of PIVKA-II in blood has previously been analyzed in detail with focus on the carboxylation site and been indicated to be rich in molecular diversity. However, the molecular diversity in the C-terminal side of PIVKA-II from the kringle domains, excluding the Glu-Gla region, has neither been studied so far nor described at all in Patent Documents 1 to 3.

PRIOR ART DOCUMENTS

Patent Documents

Patent Document 1: JP S60-60557 A
Patent Document 2: JP H05-249108 A
Patent Document 3: JP 2014-35278 A

SUMMARY OF THE INVENTION

Problem to be Solved by the Invention

An object of the present invention is to provide a means of allowing the construction of a more accurate PIVKA-II immunoassay system using monoclonal antibodies against human prothrombin.

Means for Solving the Problems

The inventors intensively studied on PIVKA-II immunoassay system using an anti-human prothrombin monoclonal antibody, and found that measurement results might vary depending on combinations of samples and anti-human prothrombin monoclonal antibodies, which suggested the potential presence of a sample (patient) of which PIVKA-II failed to be accurately measured by a conventional technique.

The inventor intensively studied further and found that there were multiple types of PIVKA-II molecules with different levels of hydrophobicity, in addition to different forms of molecular diversity in the Glu-Gla region. The ratio of multiple types of PIVKA-II molecules with different levels of hydrophobicity in a sample did not vary depending on the type of a sample (plasma or serum) but from sample to sample; for example, the ratio of PIVKA-II molecules with different levels of hydrophobicity varied even among serum samples. Furthermore, although there are multiple known anti-human prothrombin monoclonal antibodies, it was found that these monoclonal antibodies differed in affinity for PIVKA-II molecules with different levels of hydrophobicity and that there were antibodies having high affinity for PIVKA-II molecules with a high level of hydrophobicity and antibodies having high affinity for PIVKA-II molecules with a low level of hydrophobicity. For example, when an antibody that recognizes PIVKA-II molecules with a high level of hydrophobicity was used in an immunological assay method, the majority of PIVKA-II molecules in a sample containing a lot of PIVKA-II molecules with a high level of hydrophilicity were not detected, indicating that PIVKA-II in blood failed to be accurately measured.

Then, the inventors found, in the establishment of a PIVKA-II assay system using monoclonal antibodies that recognizes the prothrombin region, that the measurement of PIVKA-II with very high accuracy was enabled by measuring PIVKA-II using a mixture of an antibody having affinity for PIVKA-II molecules with a high level of hydrophobicity and an antibody having affinity for PIVKA-II molecules with a low level of hydrophobicity, and completed the present invention.

That is, the present invention provides a PIVKA-II assay method, the method comprising measuring PIVKA-II in a sample by an immunoassay using an anti-PIVKA-II antibody or antigen-binding fragment thereof which specifically binds to PIVKA-II and a mixture of at least one first anti-prothrombin antibody or antigen-binding fragment thereof and at least one second anti-prothrombin antibody or antigen-binding fragment thereof, wherein said first anti-prothrombin antibody or antigen-binding fragment thereof recognizes hydrophilic PIVKA-II molecules and wherein said second anti-prothrombin antibody or antigen-binding fragment thereof recognizes hydrophobic PIVKA-II molecules. The present invention also provides a method for production of an immunoassay reagent or kit for PIVKA-II, the method comprising the steps of: examining antibodies or antigen-binding fragments thereof that bind to both PIVKA-II and prothrombin but do not show the reactivity with thrombin for the reactivity with hydrophilic and hydrophobic PIVKA-II fractions; and mixing at least one antibody or an antigen-binding fragment thereof that reacts with the hydrophilic fractions and at least one antibody or an antigen-binding fragment thereof that reacts with the hydrophobic fractions.

Effect of the Invention

According to the present invention, a group of PIVKA-II molecules contained in a blood sample can be measured with high accuracy. It was first discovered by the inventors that PIVKA-II molecules in blood constituted a population of PIVKA-II molecules with different levels of hydrophobicity, and that the abundance of PIVKA-II molecules with a high level of hydrophobicity and PIVKA-II molecules with a low level of hydrophobicity varied from sample to sample. In an immunoassay using conventional anti-prothrombin monoclonal antibodies which had not been thoroughly investigated with respect to the hydrophobicity/hydrophilicity levels of PIVKA-II molecules in blood, a group of PIVKA-II molecules in blood failed to be accurately measured depending on the properties of antibodies used. The method of the present invention can accurately detect multiple types of PIVKA-II molecules which may be potentially overlooked by a conventional method, and thus drastically increases the accuracy of the measurement of PIVKA-II.

BRIEF DESCRIPTION OF THE DRAWINGS

FIG. 2-1 shows the result of measuring PIVKA-II molecules in a sample by using labeled antibodies A to D, where each of the fractions obtained by fractionating a serum sample (No. 4) derived from a patient with hepatocellular carcinoma by hydrophobic interaction chromatography was used as a test measurement sample.

FIG. 2-2 shows the result of measuring PIVKA-II molecules in a sample by using labeled antibodies A to D, where each of the fractions obtained by fractionating a serum sample (No. 269) derived from a patient with hepatocellular carcinoma by hydrophobic interaction chromatography was used as a test measurement sample.

FIG. 2-3 shows the result of measuring PIVKA-II molecules in a sample by using labeled antibodies A to D, where each of the fractions obtained by fractionating a serum sample (No. 275) derived from a patient with hepatocellular carcinoma by hydrophobic interaction chromatography was used as a test measurement sample.

FIG. 3-1 shows the result of measuring PIVKA-II in a sample by using an antibody mixture (antibodies C/A, antibodies C/B, or antibodies C/D) as a labeled antibody, where each of the fractions obtained by fractionating a serum sample (No. 4) derived from a patient with hepatocellular carcinoma by hydrophobic interaction chromatography was used as a test measurement sample.

FIG. 3-2 shows the result of measuring PIVKA-II in a sample by using an antibody mixture (antibodies C/A, antibodies C/B, or antibodies C/D) as a labeled antibody, where each of the fractions obtained by fractionating a serum sample (No. 269) derived from a patient with hepatocellular carcinoma by hydrophobic interaction chromatography was used as a test measurement sample.

FIG. 3-3 shows the result of measuring PIVKA-II in a sample by using an antibody mixture (antibodies C/A, antibodies C/B, or antibodies C/D) as a labeled antibody, where each of the fractions obtained by fractionating a serum sample (No. 275) derived from a patient with hepatocellular carcinoma by hydrophobic interaction chromatography was used as a test measurement sample.

FIG. 4-1 shows the result of measuring PIVKA-II in a sample by using each of antibody mixtures of Antibody C and Antibody A in various weight ratios (A:C=1:1 to 30:1) as a labeled antibody, where each of the fractions obtained by fractionating a serum sample (No. 275) derived from a patient with hepatocellular carcinoma by hydrophobic interaction chromatography was used as a test measurement sample.

FIG. 4-2 shows the result of measuring PIVKA-II in a sample by using each of antibody mixtures of Antibody C and Antibody A in various weight ratios (A:C=3:1 to 0.03:1) as a labeled antibody, where each of the fractions obtained by fractionating a serum sample (No. 275) derived from a patient with hepatocellular carcinoma by hydrophobic interaction chromatography was used as a test measurement sample.

MODE FOR CARRYING OUT THE INVENTION

Figure 1:
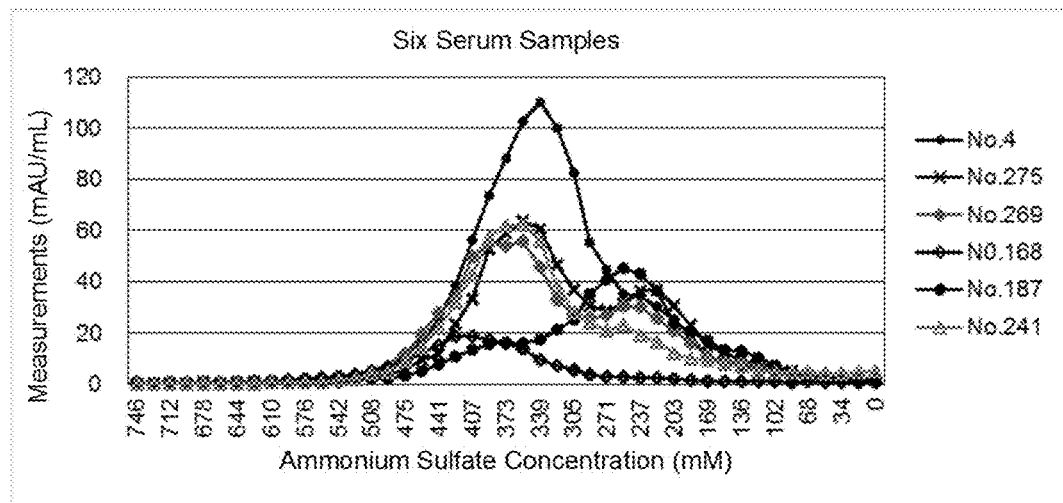
FIG. 1 shows the result of measuring PIVKA-II molecules in samples by using an ALP-labeled anti-prothrombin polyclonal antibody as an enzyme-labeled antibody, where each of the fractions obtained by fractionating each of six serum samples derived from patients with hepatocellular carcinoma by hydrophobic interaction chromatography was used as a test measurement sample.

The PIVKA-II assay method according to the present invention is a method of immunologically measuring PIVKA-II by means of antibodies or antigen-binding fragments thereof that bind to PIVKA-II, in which a mixture of at least one anti-prothrombin antibody or an antigen-binding fragment thereof that recognizes hydrophilic PIVKA-II molecules (i.e. PIVKA-II molecules with a low level of hydrophobicity) and at least one anti-prothrombin antibody or an antigen-binding fragment thereof that recognizes hydrophobic PIVKA-II molecules (i.e. PIVKA-II molecules with a high level of hydrophobicity) is used as one of the antibodies or antigen-binding fragments thereof. In the present invention, for convenience, the former antibody that recognizes hydrophilic PIVKA-II molecules is referred to as the first antibody, while the latter antibody that recognizes hydrophobic PIVKA-II molecules is referred to as the second antibody.

It was first discovered by the inventors that PIVKA-II molecules with different levels of hydrophobicity were mixed in a sample. It is assumed that the difference in hydrophobicity of PIVKA-II molecules is not derived from the difference in the extent of γ-carboxylation in the Glu-Gla region but from the structural diversity in the kringle domains within the middle region of the molecule and in the C-terminal region beyond the kringle domains.

The term "anti-prothrombin antibody" refers to an antibody which recognizes and binds to both PIVKA-II and prothrombin but does not show the reactivity with thrombin. The phrase "does not show the reactivity" as used herein means that the binding of an antibody to thrombin is not detectable (i.e., its binding to thrombin is at a level below background), or detectable but obviously weaker than its binding to PIVKA-II and prothrombin, so that those skilled in the art will conclude that binding of the antibody to thrombin does not occur. The anti-prothrombin antibody per se is known and commercial anti-prothrombin antibodies are also available. The first and second anti-prothrombin antibodies used in the present invention may be selected from known anti-prothrombin antibodies or from newly produced anti-prothrombin antibodies. The method to select first and second anti-prothrombin antibodies will be described in detail below.

Furthermore, an anti-PIVKA-II antibody or an antigen-binding fragment thereof which distinguishes PIVKA-II from prothrombin and specifically binds to PIVKA-II is used as another antibody or another antigen-binding fragment thereof. The specificity of the anti-PIVKA-II antibody can be expressed as "the antibody that binds to only PIVKA-II and does not show the reactivity with prothrombin". The meaning of the phrase "does not show the reactivity" is as described above. The anti-PIVKA-II antibody is an antibody that recognizes a region which is characteristic of PIVKA-II and absent in prothrombin, that is, the Glu-Gla region, and binds to, whether hydrophobic or hydrophilic, PIVKA-II molecules.

Such an anti-PIVKA-II antibody is also known (for example, from Patent Document 1) and commercial anti-PIVKA-II antibodies are also available. Moreover, a newly produced anti-PIVKA-II antibody may also be used.

The first and second anti-prothrombin antibodies and the anti-PIVKA-II antibody may be polyclonal antibodies or monoclonal antibodies, and are preferably monoclonal antibodies in terms of the reproducibility etc. of the immunoassay.

The methods of producing an antibody and an antigen-binding fragment thereof per se are well-known commonly used methods. An anti-prothrombin polyclonal antibody can be obtained, for example, by immunizing an animal (excluding human) with prothrombin or its partial fragment (a partial fragment outside the Glu-Gla region) together with an adjuvant as necessary, collecting blood from the animal to obtain an antiserum, and purifying the polyclonal antibody of interest in the antiserum. The immunization is typically carried out multiple times over several weeks to raise the antibody titer in the immunized animal. The antibody in the antiserum can be purified, for example, by fractionation based on ammonium sulfate precipitation or anion chromatography, affinity column purification, or the like.

An anti-prothrombin monoclonal antibody can be produced, for example, by a well-known hybridoma method. Specifically, an anti-prothrombin monoclonal antibody can be obtained by immunizing an animal (excluding human) with prothrombin or its partial fragment (a partial fragment outside the Glu-Gla region) together with an adjuvant as necessary, collecting antibody-producing cells such as splenocytes or lymphocytes from the animal, preparing hybridomas by the fusion of those cells with myeloma cells, selecting a hybridoma capable of producing an antibody that binds to prothrombin, and culturing the hybridoma and collecting the culture supernatant to obtain the antibody of interest. In the selection of the hybridoma, PIVKA-II may be used as an antigen, or the binding to both prothrombin and PIVKA-II may be confirmed.

The anti-PIVKA-II antibody can be produced by using, as an immunogen, a partial fragment containing the Glu-Gla region where carboxylation is incomplete. In the present invention, a monoclonal antibody is usually used because the antibody is required to have a sufficient specificity to PIVKA-II. The anti-PIVKA-II monoclonal antibody can be prepared by using PIVKA-II or its partial fragment (a partial fragment containing at least a part of 10 residues in the Glu-Gla region, which undergo carboxylation) as an immunogen to prepare hybridomas, selecting a hybridoma producing an antibody that binds to PIVKA-II but not to prothrombin, and then collecting the antibody. Specific examples of the production method for the anti-PIVKA-II antibody include methods described in JP S60-60557 A and JP H09-249699 A.

The "antigen-binding fragment" may be any antibody fragment as long as it retains the binding activity to the antigen (antigen-antibody reactivity) of the original antibody. Specific examples of the antigen-binding fragment include, but are not limited to, Fab, F(ab')$_2$, scFv, and the like. Fab and F(ab')$_2$ fragments can be obtained, as known well, by treating a monoclonal antibody with a protein degradation enzyme such as papain or pepsin. The production method for scFv (single chain fragment of variable region, single-chain antibody) is also well known. A scFv fragment can be obtained, for example, by extracting mRNA from the hybridoma produced as described above to prepare single-stranded cDNA; amplifying the immunoglobulin H chain gene and L chain gene therefrom by PCR using immunoglobulin H chain-specific and L chain-specific primers; connecting the amplified fragments by a linker; adding appropriate restriction enzyme sites to it; introducing it into a plasmid vector; transforming *E. coli* bacteria with this vector to express scFv fragment; and recovering the scFv fragment from the *E. coli* bacteria.

A polypeptide or its partial fragment used as the immunogen can be produced by commonly used methods such as chemical synthesis, genetic engineering techniques, and the like. Or, the polypeptide or its partial fragment can also be obtained by extracting and purifying prothrombin or PIVKA-II from fresh human plasma and the like (see, Thromb. Diath. Haemorph., 1966; 16: 469-90; and the like).

The amino acid sequence shown in SEQ ID NO: 1 in the Sequence Listing is an amino acid sequence composed of the sequence shared by prothrombin and PIVKA-II and a signal sequence added thereto, in which the region from amino acid 44 to amino acid 622 corresponds to the amino acid sequence shared by prothrombin and PIVKA-II. The region from amino acid 44 to amino acid 84 is the Glu-Gla region, and in prothrombin, all of the ten "Xaa" residues in this region are γ-carboxyglutamic acid (Gla) residues. This prothrombin sequence is deposited in GenBank under accession No. NP_000497. The base sequence shown in SEQ ID NO: 2 is a sequence encoding the amino acid sequence of SEQ ID NO: 1 and is deposited in GenBank under accession No. NM_000506. The region from base 44 to base 1912 in SEQ ID NO: 2 is a coding region.

Specific examples of the chemical synthesis method include the Fmoc method (the fluorenylmethyloxycarbonyl method), the tBoc method (the t-butyloxycarbonyl method), and the like. Moreover, the synthesis may also be carried out using various commercially available peptide synthesizers by a conventional method. In the case of chemical synthesis, a desired polypeptide can be synthesized based only on its amino acid sequence.

Methods of producing a polypeptide by genetic engineering techniques are also well known. When a polypeptide to be used as an immunogen in the production of an anti-prothrombin antibody is produced by genetic engineering techniques, the production of the polypeptide may be carried out, for example, as follows. First, RNA is extracted from human-derived culture cells and the like, and cDNA is synthesized from the mRNA by reverse transcription reaction. Using this cDNA as a template and using primers designed based on the mRNA sequence information of human prothrombin, PCR is carried out to prepare a polynucleotide encoding the full-length of or a desired part of prothrombin. The primers used in PCR can be appropriately designed based on the base sequence shown in SEQ ID NO: 2 or the sequence information of human prothrombin deposited in a database such as GenBank. Or, a polynucleotide encoding a desired polypeptide can also be prepared by a conventional method using a commercially available nucleic acid synthesizer. Since codons coding for the respective amino acids are known, if an amino acid sequence can be specified, the base sequence of a polynucleotide encoding the amino acid sequence can also be determined. Then, the prepared polynucleotide is incorporated into an appropriate vector to express the polypeptide in an appropriate expression system, and the expressed polypeptide is recovered, and thereby the desired polypeptide can be obtained. The vectors and various expression systems (bacterial expression system, yeast cell expression system, mammalian cell expression system, insect cell expression system, cell-free expression system, and the like) to be used are also well known, and various vectors, host cells, reagents, and kits are commercially available. Therefore, those skilled in the art can select and use appropriate ones. Human-derived cultured cells are also commercially available or distributed, and thus can be easily obtained.

In the present invention, immunoassay of PIVKA-II is typically carried out by a sandwich method. The sandwich immunoassay per se is a well-known, commonly used method. Specific examples of the sandwich immunoassay include chemiluminescent enzyme immunoassay (CLEIA), enzyme-linked immunosorbent assay (ELISA), radio-immunoassay, electrochemiluminescence immunoassay, and the like. Any of those methods may be used in the present invention.

In the sandwich assay system, usually, one of two kinds of antibodies or antigen-binding fragments thereof is immobilized on a solid phase to use it as an immobilized antibody, and the other is labeled with a labeling substance to use it as a labeled antibody. In the present invention, a mixture of the first and second anti-prothrombin antibodies or antigen-binding fragments thereof is used as a single antibody, and an anti-PIVKA-II antibody or an antigen-binding fragment thereof is used as another antibody, either of which may be used as an immobilized antibody. In the Examples below, the anti-PIVKA-II antibody is used as an immobilized antibody, and the antibody mixture is used as a labeled antibody. However, the present invention is not limited thereto.

The PIVKA-II assay method according to the present invention will be specifically described by way of an example hereinbelow, where a mixture of the first and second anti-prothrombin antibodies is used as a labeled antibody. Of course, the mixture can be used as an immobilized antibody, while an anti-PIVKA-II antibody can be used as a labeled antibody. Thus, the present invention is not limited to the specific example below. Moreover, antigen-binding fragments of the respective antibodies may be used instead of the antibodies.

First, an anti-PIVKA-II antibody (immobilized antibody) is immobilized on a carrier. The immobilized anti-PIVKA-II antibody and PIVKA-II contained in a sample are allowed to contact each other to allow specific binding between the immobilized antibody and PIVKA-II. Then, unbound components in the sample are removed, for example, by washing the carrier with an appropriate buffer, and a mixture of the first and second anti-prothrombin antibodies labeled with a labeling substance (that is, a mixture of at least one first labeled anti-prothrombin antibody and at least one second labeled anti-prothrombin antibody) is subsequently allowed to bind to the PIVKA-II bound to the immobilized antibody. After completion of the reaction, unreacted components are removed, for example, by washing the carrier with an appropriate buffer, and a signal from the labeling substance is subsequently detected by an appropriate method, and thereby the PIVKA-II contained in the sample can be measured.

The solid phase is not particularly limited, and it may be the same as a solid phase used in a known sandwich immunoassay system. Specific examples of the material of the solid phase include, but are not limited to, polystyrene, polyethylene, sepharose, and the like. The physical form of the solid phase is essentially not important. The solid phase to be used is preferably such a solid phase that an antibody is easily immobilized on its surface and the immune complex formed during the assay is easily separated from unreacted components. In particular, a solid phase such as plastic plate or magnetic particle used in a conventional immunoassay is preferable. Magnetic particles of materials as described above are most preferably used in terms of ease of handling, storage, separation, and the like. An antibody can be bound to these solid phases by a commonly used method well-known to those skilled in the art. The binding of the antibody to a solid phase may be achieved by physical adsorption or by means of covalent coupling. For example, the glutaraldehyde method, the periodic acid method, the maleimide method, the pyridyl disulfide method, and the like can be used. Or, antibody-bound particles can be obtained by adding and dispersing magnetic particles in a buffer to prepare a particle suspension, adding an appropriate amount of the antibody to the particle suspension, stirring the suspension at a temperature from 20 to 37° C. for one hour, and then collecting the magnetic particles by magnetic force and washing the particles with an appropriate buffer. The composition of the buffer to be used may be the same as that of a common buffer used in the immobilization of antibodies. The pH of the buffer may be in such a range that the antibody can stably exist in the buffer and the immobilization of the antibody on a solid phase is not inhibited.

The labeling substance is also not particularly limited, and a labeling substance similar to those used in known immunoassay systems may be used. Specific examples of the labeling substance include enzymes, fluorescent substances, chemiluminescent substances, staining substances, radioactive substances, and the like. Examples of the enzymes that may be used include, but are not limited to, known enzymes such as alkaline phosphatase (ALP), peroxidase, β-galactosidase, and the like. ALP is desirably used to provide an assay system with high detection sensitivity. The antibody can be bound to these labeling substances by a commonly used method well-known to those skilled in the art. The binding of the antibody to a labeling substance is preferably achieved by covalent coupling, and the glutaraldehyde method, the periodic acid method, the maleimide method, the pyridyl disulfide method, and the like can be used. For example, an antibody labeled with a labeling substance can be prepared by mixing a maleimide-modified ALP and an antibody fragment derived from an antibody treated with pepsin and then reduced.

In cases where an enzyme is used as a labeling substance, an object of measurement can be measured by allowing the enzyme to react with a corresponding substrate, such as a coloring substrate, fluorescent substrate, or luminescent substrate, and measuring the resulting signal to determine the activity of the enzyme. For example, when an ALP is used as a labeling substance, a luminescent substrate such as disodium 3-(4-methoxyspiro(1,2-dioxetane-3,2'-tricyclo[3.3.1.13,7]decan)-4-yl)phenyl phosphate (for example, AMPPD (trade name)) may be used.

In cases where biotin or a hapten is used as a labeling substance, measurement can be carried out using streptavidin, an antibody against the hapten, or the like, to which an enzyme, fluorescent substance, chemiluminescent substance, staining substance, radioactive substance, or the like is coupled.

The means of detecting the signal is appropriately selected depending on the type of the labeling substance. For example, a colorimeter or absorption meter, a fluorophotometer, a photon counter, and a radiation meter may be used in cases where the signal is coloring, fluorescence, luminescence, and radiation, respectively. The amount of PIVKA-II in a sample can be determined as follows: standard samples containing various known concentrations of PIVKA-II are measured according to the method of the present invention, and the correlation between the value of signal derived from the label and the concentrations of PIVKA-II in the standard samples is plotted to generate a standard curve, and the same measurement procedure is performed on a sample containing an unknown concentration of PIVKA-II to determine the value of signal from the label, and the determined value of signal is applied to the standard curve to obtain the concentration of PIVKA-II.

The sample to which the assay method of the present invention is applied is a sample separated from a subject, preferably a blood sample, and particularly preferably plasma or serum. The sample may be diluted as required before use.

The subject is not particularly limited as long as it is a mammal. The subject is generally a human, and may be, for example, a patient with hepatocellular carcinoma or a patient suspected of having hepatocellular carcinoma.

The first and second anti-prothrombin antibodies used in the immunoassay for PIVKA-II according to the present invention are at least one anti-prothrombin antibody that recognizes hydrophilic PIVKA-II molecules and at least one anti-prothrombin antibody that recognizes hydrophobic PIVKA-II molecules, respectively, as described above. It may be determined whether a known anti-prothrombin antibody or a newly prepared anti-prothrombin antibody has affinity for either hydrophilic PIVKA-II molecules or hydrophobic PIVKA-II molecules, by performing a sandwich immunoassay using the anti-prothrombin antibody and an anti-PIVKA-II antibody with a set of fractions each obtained by fractionating a sample containing PIVKA-II by hydrophobic interaction chromatography, which fractions are used as test measurement samples, and investigating with which of the fractions the known anti-prothrombin antibody or the newly prepared anti-prothrombin antibody has a higher reactivity.

As a sample containing PIVKA-II which is used for preparation of the test measurement sample, for example, a serum and the like which are derived from a patient with hepatocellular carcinoma may be used. In the hydrophobic interaction chromatography, a hydrophobic chromatography column employing phenyl group as a functional group may be used, and elution may be carried out with a linear concentration gradient of ammonium sulfate (for example, 1.0 M→0 M). Around 20 to 30 elution fractions may be collected and a set of the obtained elution fractions may be used as a set of the test measurement samples. In cases where multiple patient-derived sera are used as PIVKA-II-containing samples, the sera may be individually subjected to chromatography to prepare multiple sets of test measurement samples, or the multiple serum samples may be mixed and then subjected to chromatography to prepare a set of test measurement samples.

Individual fractions included in the test measurement samples prepared as described above are measured by means of a sandwich immunoassay using an anti-prothrombin antibody, which should be investigated for its affinity for hydrophobic and hydrophilic PIVKA-II molecules, and an anti-PIVKA-II antibody. The sandwich immunoassay system can be constructed in the same way as the PIVKA-II immunoassay system is ultimately constructed. Namely, in cases where a PIVKA-II immunoassay system using a mixture of first and second anti-prothrombin antibodies as a labeled antibody and the anti-PIVKA-II antibody as an immobilized antibody is constructed, the above-described test measurement samples may be measured using the anti-prothrombin antibody, which should be investigated for its affinity for hydrophobic and hydrophilic PIVKA-II molecules, as a labeled antibody and the anti-PIVKA-II antibody as an immobilized antibody.

PIVKA-II molecules with a low level of hydrophobicity (i.e. hydrophilic PIVKA-II molecules) are contained in elution fractions containing a high concentration of ammonium sulfate, and PIVKA-II molecules with a high level of hydrophobicity (i.e. hydrophobic PIVKA-II molecules) are contained in elution fractions containing a low concentration of ammonium sulfate. In the present invention, the former elution fractions are referred to as hydrophilic PIVKA-II fractions and the latter elution fractions are referred to as hydrophobic PIVKA-II fractions. By investigating the reactivity of an anti-prothrombin antibody with these elution fractions, it can be determined whether the anti-prothrombin antibody has affinity for (recognizes) either hydrophilic PIVKA-II molecules or hydrophobic PIVKA-II molecules.

The concentration of ammonium sulfate to differentiate between the hydrophilic and hydrophobic PIVKA-II fractions can usually be selected from the range of 270 mM to 370 mM, such as 290 mM to 350 mM, 300 mM to 340 mM, 310 mM to 330 mM, 280 mM to 330 mM, or 290 mM to 330 mM. Elution fractions containing ammonium sulfate at a concentration equal to or greater than a concentration selected from those ranges may be used as hydrophilic PIVKA-II fractions, while elution fractions containing ammonium sulfate at a concentration less than the selected concentration may be used as hydrophobic PIVKA-II fractions.

To prepare hydrophilic and hydrophobic PIVKA-II fractions used when an anti-prothrombin antibody is investigated for its affinity, at least one sample containing both hydrophilic PIVKA-II and hydrophobic PIVKA-II molecules, or at least two samples including at least one sample containing at least hydrophilic PIVKA-II molecules and at least one sample containing at least hydrophobic PIVKA-II molecules are required. Whether an arbitrary sample contains either hydrophilic PIVKA-II molecules or hydrophobic PIVKA-II molecules can be determined, for example, by a sandwich immunoassay using an anti-PIVKA-II antibody and an anti-prothrombin polyclonal antibody. When a sample appropriately containing both hydrophilic PIVKA-II and hydrophobic PIVKA-II molecules is not available, the test measurement samples may be prepared by using multiple samples, as described above.

After determining the reactivity with the hydrophilic fractions and the hydrophobic fractions, the concentrations of ammonium sulfate and the signal values obtained by the immunoassay are plotted on the horizontal axis and the vertical axis, respectively, to indicate the reactivity with each fraction (the detected signal intensity). The signal values may be plotted without any modification or with calculating the ratio of signal intensity in each elution fraction to the total activity. When an anti-prothrombin antibody has a higher reactivity with the hydrophilic fractions, the anti-prothrombin antibody is determined to be an antibody having affinity for hydrophilic PIVKA-II molecules. When an anti-prothrombin antibody has a higher reactivity with the hydrophobic fractions, the anti-prothrombin antibody is determined to be an antibody having affinity for hydrophobic PIVKA-II molecules.

The mixing ratio between the first antibody and the second antibody may be within such a range that both hydrophobic PIVKA-II molecules and hydrophilic PIVKA-II molecules in a sample can be measured. The mixing ratio is not particularly limited, but it may be set in such a way that a ratio between peak heights or peak areas ranges from 1:10 to 10:1, for example, from 1:5 to 5:1, from 1:3 to 3:1, or from 1:2 to 2:1, where the peak heights or peak areas are obtained by plotting the signal values or the ratios of signal intensities to the total activity of the respective fractions derived from a PIVKA-II-containing sample as described above. The mixing ratio by weight between the first antibody and the second antibody (in cases where multiple antibodies are used for the respective antibodies, it is a ratio between the total amount of the first antibodies and the total amount of the second antibodies) may be set within such a range that both hydrophobic PIVKA-II molecules and hydrophilic PIVKA-II molecules in a sample can be measured, depending on the affinity of each antibody for PIVKA-II. A preferable mixing ratio by weight between the first antibody and the second antibody is not particularly limited because it can vary depending on the strength of affinity of the first antibody for hydrophilic PIVKA-II molecules and the strength of affinity of the second antibody for hydrophobic PIVKA-II molecules. However, the ratio between peak heights or peak areas within the above-described range can often be achieved by setting the mixing ratio by weight between the antibodies within the range from 0.03:1 to 30:1, for example, from 0.05:1 to 20:1, from 0.1:1 to 10:1, or from 0.3:1 to 3:1. Accurate measurement of various types of PIVKA-II molecules present in a sample is enabled by combining at least one anti-prothrombin antibody that has affinity for and recognizes hydrophilic PIVKA-II molecules (a first antibody) and at least one anti-prothrombin antibody that has affinity for and recognizes hydrophobic PIVKA-II molecules (a second antibody) and using a mixture of both the antibodies as an immobilized antibody or labeled antibody.

A PIVKA-II immunoassay reagent or kit to perform the PIVKA-II assay method according to the present invention can be produced by the steps below.

(Step 1) Antibodies that bind to both PIVKA-II and prothrombin but do not show the reactivity with thrombin (anti-prothrombin antibodies) or antigen-binding fragments thereof are examined for their reactivity with hydrophilic and hydrophobic PIVKA-II fractions.

(Step 2) At least one antibody or an antigen-binding fragment thereof that reacts with the hydrophilic fractions is mixed with at least one antibody or an antigen-binding fragment thereof that reacts with the hydrophobic fractions.

The anti-prothrombin antibodies or antigen-binding fragments thereof to be subjected to Step 1 may be known anti-prothrombin antibodies or antigen-binding fragments thereof, or may be anti-prothrombin antibodies newly prepared as antibodies that bind to both PIVKA-II and prothrombin but do not show the reactivity with thrombin, or antigen-binding fragments thereof. The method of examining antibodies for the reactivity with hydrophilic and hydrophobic PIVKA-II fractions is as described above.

An antibody that reacts with hydrophilic PIVKA-II fractions and an antibody that reacts with hydrophobic PIVKA-II fractions respectively correspond to a first anti-prothrombin antibody and a second anti-prothrombin antibody referred to in the present specification. A mixture of at least one first anti-prothrombin antibody or an antigen-binding fragment thereof and at least one second anti-prothrombin antibody or an antigen-binding fragment thereof can be provided as an immunoassay reagent or kit in a conjugated form with a labeling substance, or in an immobilized form on a solid phase such as plastic plate or magnetic particles. Thus, the production method for the immunoassay reagent or kit can further comprise the step of labeling the anti-prothrombin antibodies or the antigen-binding fragments thereof with a labeling substance before Step 1, or after Step 1, or after mixing the first and second antibodies or the antigen-binding fragments thereof in Step 2, or, the step of immobilizing the anti-prothrombin antibodies or the antigen-binding fragments thereof on a solid phase after Step 2. In cases where the anti-prothrombin antibodies or the antigen-binding fragments thereof are immobilized on particles as a solid phase, such as magnetic particles, the immobilization process may be carried out before Step 1 or after Step 1, and thereafter, those particles with the respective immobilized antibodies may be mixed in Step 2.

An immunoassay reagent produced by the above-described method may be a reagent consisting only of a mixture of the first and second antibodies or antigen-binding fragments thereof, or may have a form of the mixture dissolved in an appropriate buffer, and may further contain useful ingredients, such as ingredients for stabilizing the antibodies:

Moreover, a combination of the above-described immunoassay reagent with an anti-PIVKA-II antibody or an antigen-binding fragment thereof can be provided as an immunoassay reagent or kit. For example, a mixture of labelled first and second anti-prothrombin antibodies or antigen-binding fragments thereof in combination with a solid phase on which anti-PIVKA-II antibody or antigen-binding fragment thereof is immobilized (or, a set of an anti-PIVKA-II antibody or an antigen-binding fragment thereof and a solid phase on which the antibody or the antigen-binding fragment thereof will be immobilized) can be provided as a PIVKA-II immunoassay kit. The antibodies to be labelled and the antibody to be immobilized may be reversed. The immunoassay kit may further include a substrate for the labeling substance, a sample diluent, a washing solution, and the like.

EXAMPLES

The present invention will be more specifically described below by way of examples. However, the present invention is not limited to the examples below.

1. Hydrophobic Interaction Chromatography

A total of 1.0 mL of a sample prepared by mixing 25 to 50 µL of a serum sample, 500 µL of 0.1 M phosphate buffer (PB), pH 7.0, containing 2 M ammonium sulfate (5.00 g/L monopotassium phosphate, 22.6 g/L disodium phosphate (12 hydrate), 264 g/L ammonium sulfate; adjusted to pH 7.0 by adding an appropriate amount of 4 N sodium hydroxide) and 450 µL to 475 µL of 0.1 M PB, pH 7.0 (5.00 g/L monopotassium phosphate, 22.6 g/L disodium phosphate (12 hydrate); adjusted to pH 7.0 by adding an appropriate amount of 4 N sodium hydroxide) was separated by chromatography.

A HiTrap Phenyl HP column (GE Healthcare; support volume: 1 mL) was used for hydrophobic interaction chromatography, and an AKTA FPLC UPC 900 instrument (GE Healthcare) was used for fractionation.

The column was equilibrated with 10 or more column volumes of 0.1 M PB, pH 7.0, containing 1 M ammonium sulfate, and 1.0 mL of the above-described sample was then injected to the column and fractionated at a flow rate of 0.5 mL. Elution fractions were collected in 0.5-ml aliquots. Elution was performed by a linear gradient of salt concentration using two solutions, which were 0.1 M PB, pH 7.0, containing 1 M ammonium sulfate (5.00 g/L monopotassium phosphate, 22.6 g/L disodium phosphate (12 hydrate), 132 g/L ammonium sulfate; prepared at pH 7.0 by adding an appropriate amount of 4 N sodium hydroxide) and 0.1 M PB, pH 7.0 (5.00 g/L monopotassium phosphate, 22.6 g/L disodium phosphate (12 hydrate); pH was adjusted as described above). The concentration of ammonium sulfate was changed from 1.0 M to 0 M while a total of 30 mL of elution fractions were eluted.

2. Preparation of Labeled Antibodies

Labeled antibodies were produced using four monoclonal antibodies that bound to both PIVKA-II and prothrombin (Antibody A, Antibody B, Antibody C, Antibody D).

A 6-mL aliquot of a 3 mg/mL solution of Antibody A was taken and applied to a G-25 column (manufactured by Pharmacia Corporation) equilibrated with 0.1 M citric acid buffer (pH 3.5) to exchange the buffer of the antibody solution. To this solution, about 100 µL of 1 mg/mL pepsin solution was added, and the resulting mixture was left to stand at 37° C. for 1 hour. After the pH was adjusted to nearly neutral with Tris buffer, the resulting solution was applied to a Superdex 200 column (manufactured by Pharmacia Corporation) for antibody purification by gel filtration. Among obtained fractions, a fraction giving a single peak of absorbance at 280 nm was pooled as the F(ab')$_2$ fragment of Antibody A. To 4 mL of this F(ab')$_2$ fragment solution, 200 µL of 0.2M 2-mercaptoethylamine (hereinafter described as 2-MEA) solution was added, and the resulting mixture was left to stand at 37° C. for 2 hours to perform reduction of the fragment. This solution was applied to a G-25 column to remove 2-MEA, thereby obtaining the Fab' fragment of Antibody A.

To a G-25 column equilibrated with 0.1 M phosphate buffer (pH 7.0), 1.5 mL of 10 mg/mL high-specific-activity ALP solution was applied, to exchange the buffer of the ALP solution. To this solution, 70 µL of 10 mg/mL N-(4-maleimidobutyryloxy)-succinimide (hereinafter described as GMBS) solution in dimethylformamide was added, and the resulting mixture was left to stand at 30° C. for 1 hour to allow the reaction to proceed. This solution was applied to a G-25 column equilibrated with 0.1 M phosphate buffer (pH6.3) to remove excess GMBS, thereby producing a maleimide-modified ALP. Four-milliliter of a solution of the previously produced Fab' fragment of Antibody A, 3 mL of a solution of the maleimide-modified ALP and 13 mL of 0.1 M phosphate buffer (pH6.3) were mixed and left to stand at room temperature for one hour to obtain an ALP-labeled antibody. To this solution, 1 mL of 2M 2-MEA solution was added, and the resulting mixture was left to stand at room temperature for 30 minutes to block excess maleimide groups, and then applied to a Superdex 200 column for purification. Among fractions giving peaks of absorbance at 280 nm, fractions in which the molar ratio between Fab' and the ALP was 1:1 were pooled, to obtain a purified ALP-labeled Antibody A.

Labeled antibodies were prepared in the same way from Antibody B, Antibody C and Antibody D.

3. Measurement of PIVKA-II

Each fraction obtained by fractionating a sample containing PIVKA-II (such as serum sample) by hydrophobic interaction chromatography as described above in Section 1 was used as a test measurement sample. The measurement was carried out using, in addition to the enzyme-labeled antibodies, accessory reagents (antibody-bound particles, PIVKA-H calibrator set) included in LUMIPULSE Presto (registered trade name) PIVKA-II Eisai (manufactured by Fujirebio Inc.), and reagents (substrate solution, washing solution, and the like) for LUMIPULSE Presto (manufactured by Fujirebio Inc.).

First, 20 µL of the test measurement sample was added to 50 µL of antibody-bound particles (anti-PIVKA-II monoclonal antibody (mouse)-conjugated ferrite particles) included in LUMIPULSE Presto PIVKA-II Eisai, which particles were conjugated with an anti-PIVKA-II monoclonal antibody (mouse) that specifically bound to PIVKA-II, and the resulting mixture was stirred and then allowed to react at 37° C. for 8 minutes. The magnetic particles were separated from the residual reaction solution by the magnetic force, and then washed with the washing solution. To the washed particles, any of the ALP-labelled Antibody A (at a final concentration of 0.36 µg/mL), Antibody B (at a final concentration of 0.5 µg/mL), Antibody C (at a final concentration of 0.12 µg/mL) and Antibody D (at a final concentration of 0.5 µg/mL), or an ALP-labeled anti-prothrombin polyclonal antibody included in LUMIPULSE Presto PIVKA-II Eisai was added, and the resulting mixture was stirred and then allowed to react at 37° C. for 8 minutes. The magnetic particles were again separated from the residual reaction solution by the magnetic force, and then washed with the washing solution. To the particles, 200 µL of the substrate solution containing 3-(2'-spiroadamantane)-4- methoxy-4-(3"-phosphoryloxy)phenyl-1,2-dioxetane disodium salt (AMPPD), which is a chemiluminescent substrate for alkaline phosphatase, was added, and the resulting mixture was allowed to react at 37° C. for 4 minutes. The amount of chemiluminescence (wavelength: 463 nm) after the reaction was measured with a luminometer. The fully automated chemiluminescent immunoassay instrument LUMIPULSE Presto II (manufactured by Fujirebio Inc.) was used for the measurement.

FIG. 1 shows the result of a measurement using an ALP-labeled anti-prothrombin polyclonal antibody included in LUMIPULSE Presto PIVKA-II Eisai as an enzyme-labeled antibody, where each of the fractions obtained by fractionating each of six serum samples derived from patients with hepatocellular carcinoma by hydrophobic interaction chromatography was used as a test measurement sample. The signal values of the respective fractions were converted to activity values (mAU/mL) by calculation according to the method described in the package insert of LUMIPULSE Presto PIVKA-II Eisai, and those values were plotted in a graph. Bimodal patterns with two peaks were observed in some samples and unimodal patterns with one peak were observed in other samples. Thus, various peak patterns resulted from different samples. This indicates that multiple PIVKA-II molecules with different characteristics, such as more hydrophilic molecules and more hydrophobic molecules, are mixed in blood and the abundance ratio between the respective molecules varies in different blood samples. Since PIVKA-II molecules were contained in both the hydrophilic fractions and the hydrophobic fractions, it was indicated that it was essential to select monoclonal antibodies which successfully reacted with both the fractions, for the purpose of accurately measuring PIVKA-II in blood in a reproducible manner.

Figures 1, 2:
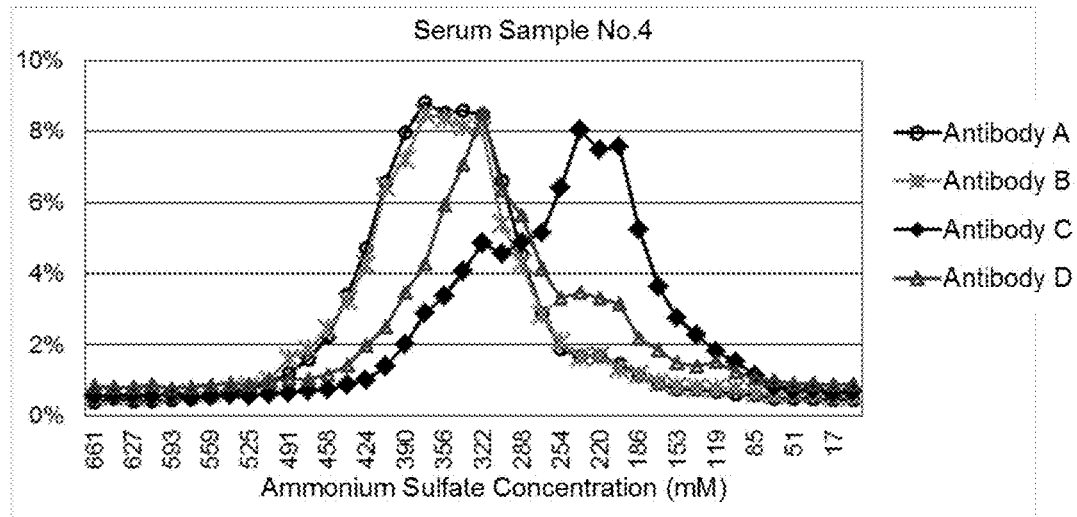
Figure 2:
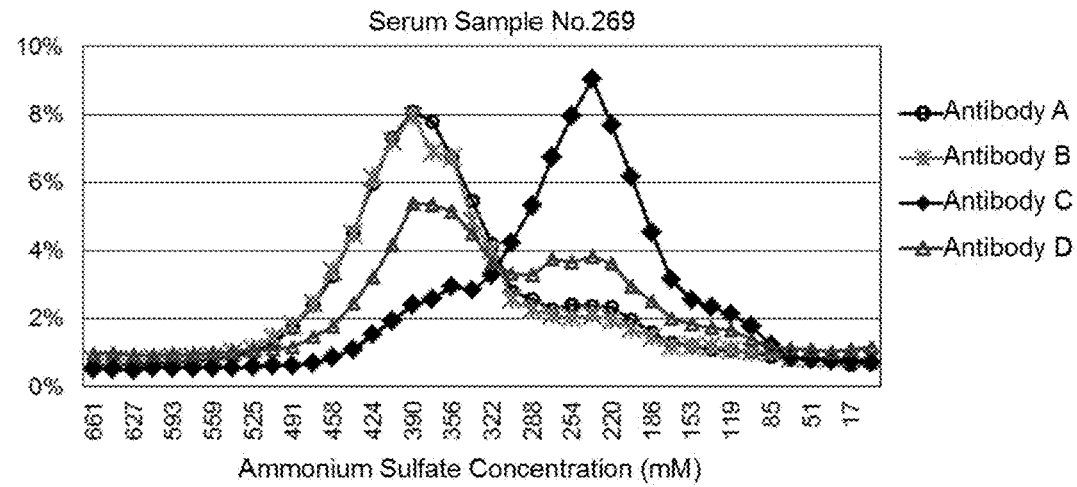
Figures 2, 3:
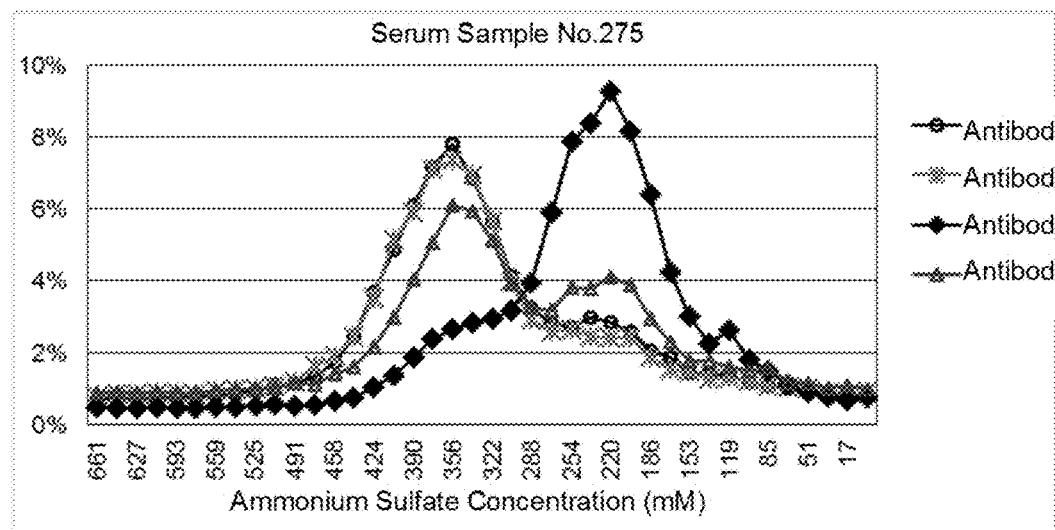
Figures 1, 3:
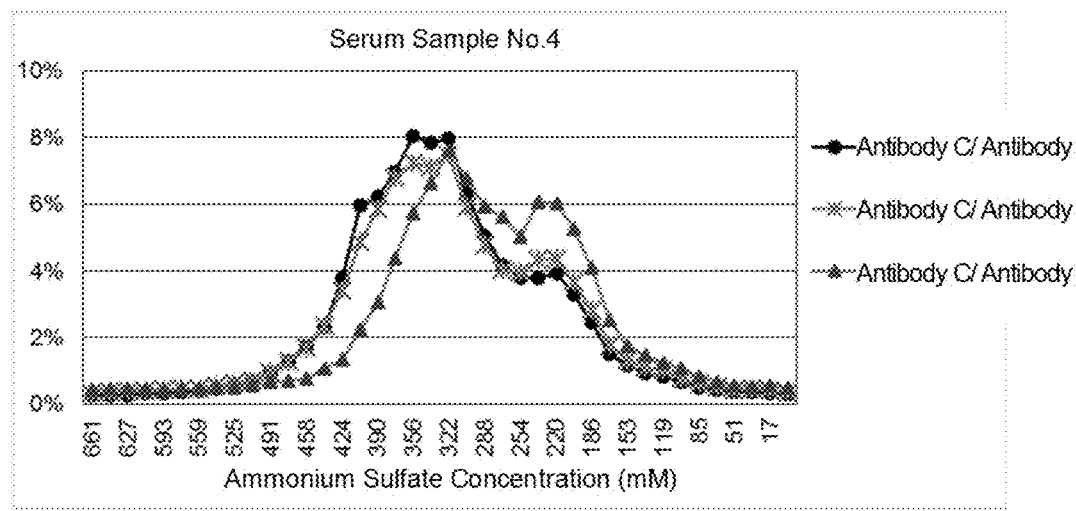
Figures 2, 3:
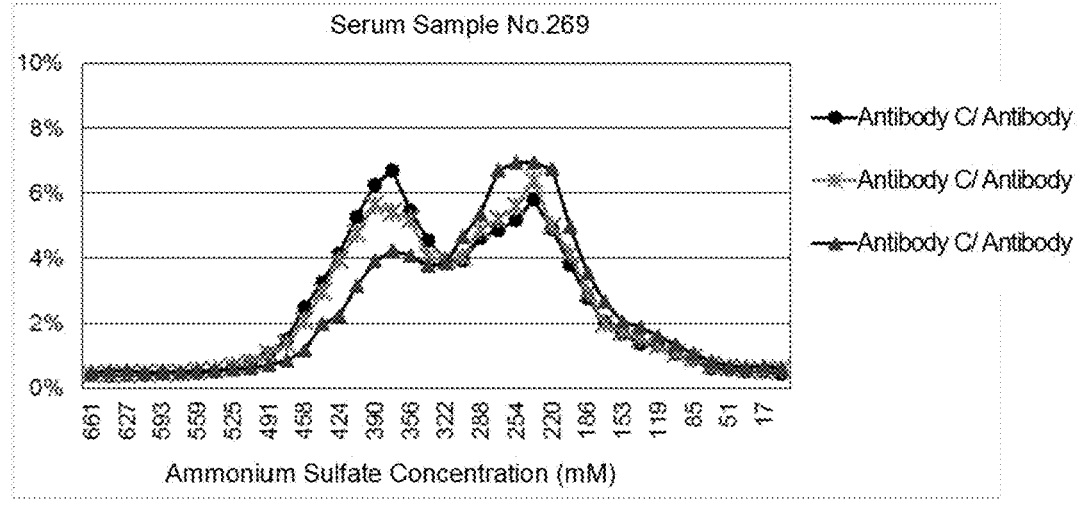
Figure 3:
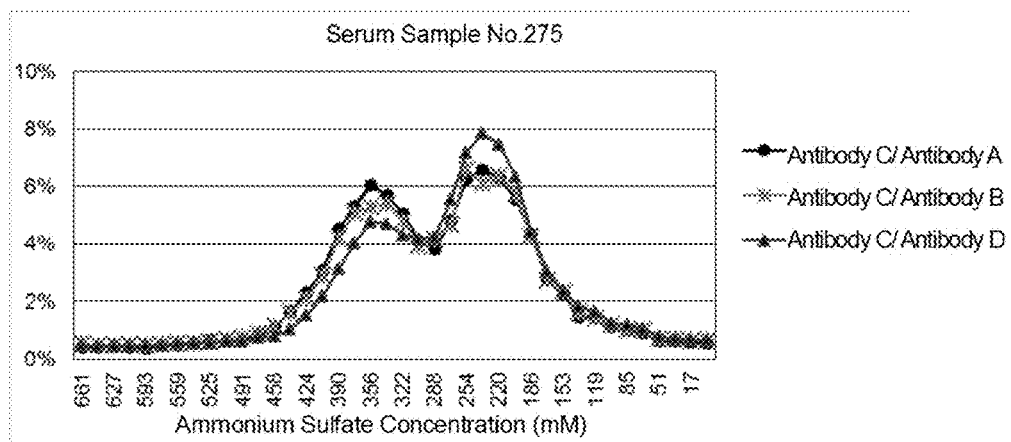

FIGS. 2-1 to 2-3 show the results of measurements using the labeled Antibodies A to D, where each of the fractions obtained by fractionating each of three serum samples (Sample No. 4, No. 269, No. 275) derived from patients with hepatocellular carcinoma by hydrophobic interaction chromatography was used as a test measurement sample. The signal values of the respective fractions were used to calculate the percentage of signal intensity in each fraction to the detected total activity (total signal values), and the calculated percentages were plotted in a graph. Antibody A and Antibody B reacted with the hydrophilic fractions, while Antibody C reacted with the hydrophobic fractions. Antibody D reacted mainly with the hydrophilic fractions and could also react with the hydrophobic fractions. Based on these results, it was suggested that use of an antibody that reacted with the hydrophilic fractions and an antibody that reacted with the hydrophobic fractions in combination made it possible to accurately measure PIVKA-II in blood.

Then, indeed, a mixture of an antibody that reacted with the hydrophilic PIVKA-II fractions (Antibody A, Antibody B, or Antibody D) and an antibody that reacted with the hydrophobic fractions (Antibody C) was used as a labeled antibody to perform a measurement on the above-described test measurement samples prepared from the three serum samples. The signal values of the respective fractions were used to calculate the percentage of signal intensity in each fraction to the detected total activity, and the calculated percentages were plotted in a graph. Labeled antibodies were prepared by mixing each of the ALP-labeled Antibody A (at a final concentration of 0.36 μg/mL), Antibody B (at a final concentration of 0.5 μg/mL) and Antibody D (at a final concentration of 0.5 μg/mL) with the ALP-labeled Antibody C (at a final concentration of 0.12 μg/mL). The results of the measurement are shown in FIGS. 3-1 to 3-3. It was confirmed that use of two different antibodies, one of which reacted with the hydrophilic fractions and the other of which reacted with the hydrophobic fractions, enabled a reaction with both the hydrophilic fractions and the hydrophobic fractions to proceed, as in the case of the anti-prothrombin polyclonal antibody.

4. Study on the Mixing Ratio Between Antibodies

Next, the mixing ratio between an antibody that reacted with the hydrophilic PIVKA-II fractions (Antibody A) and an antibody that reacted with the hydrophobic fractions (Antibody C) was studied. PIVKA-II was assayed by the same method as that described in "3. Measurement of PIVKA-II", except that the ALP-labeled Antibody A and the ALP-labeled Antibody C were mixed in ratios as indicated in Tables 1 and 2 below. The serum sample (No. 275) derived from a patient with hepatocellular carcinoma was used as a sample. The sample of No. 275 is a sample which has been confirmed to contain both hydrophilic PIVKA-II and hydrophobic PIVKA-II molecules, based on the reactivity with the anti-prothrombin polyclonal antibody (FIG. 1).

Figures 1, 4:
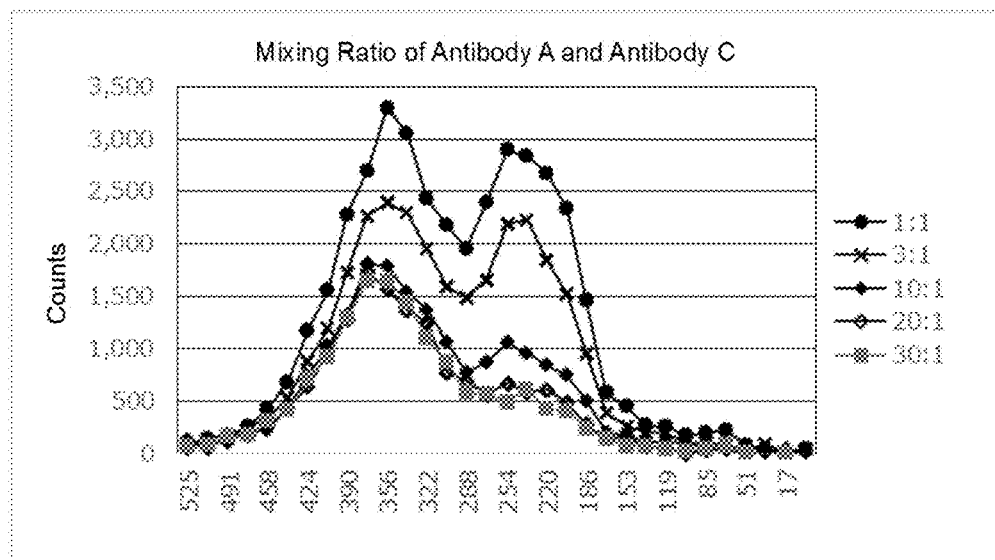
Figures 2, 4:
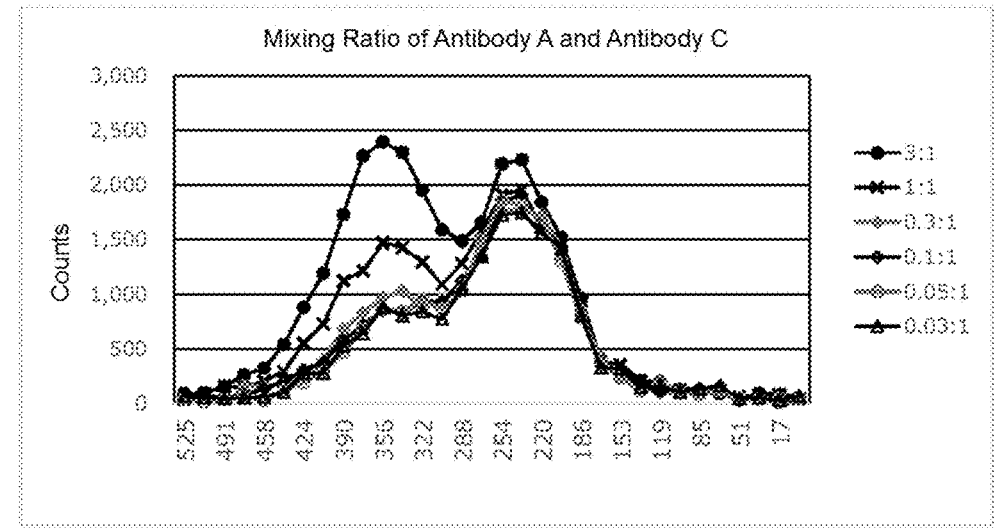

The results of the measurement are shown in FIGS. 4-1 and 4-2. The vertical axis represents the actually measured count values. Then, it was confirmed that detection of both the hydrophilic fractions and the hydrophobic fractions was possible in all the studied mixing ratios by weight (0.03:1 to 30:1).

In addition, the peak area ratio was compared between the hydrophilic fractions and the hydrophobic fractions. In this Example, an ammonium sulfate concentration between 288 mM and 305 mM was selected as a boundary to separate hydrophilic fractions and hydrophobic fractions, and the peak area of the hydrophilic fractions and the peak area of the hydrophobic fractions were calculated by adding up the count values of fractions included in the respective peaks. For the purpose of calculating the peak areas, the values from the fraction corresponding to 525 mM, which was the leading edge of the peak, to the fraction corresponding to 68 mM were used, and the count values of 14 fractions each for hydrophilic and hydrophobic fractions were added up. For the purpose of removing the background, the count value of a fraction outside the peak was subtracted from each of the count values actually counted, and the thus obtained values were used as count values in calculating the peak areas.

The peak area ratios calculated with respect to the respective mixing ratios are presented in Tables 1 and 2. The peak area ratio between the hydrophilic fractions and the hydrophobic fractions ranged from 1:2.1 to 2.8:1 when the mixing ratio of antibodies (weight ratio) ranged from 0.03:1 to 30:1, the peak area ratio ranged from 1:2.1 to 2.5:1 when the mixing ratio of antibodies ranged from 0.05:1 to 20:1, the peak area ratio ranged from 1:1.9 to 1.8:1 when the mixing ratio of antibodies ranged from 0.1:1 to 10:1, and the peak area ratio ranged from 1:1.7 to 1.2:1 when the mixing ratio of antibodies ranged from 0.3:1 to 3:1. Accordingly, it was confirmed that the combination use of Antibody A and Antibody C enabled accurate detection of both the hydrophilic and hydrophobic fractions.

TABLE 1

| Antibody Concentration (μg/mL) | | Antibody Mixing Ratio (weight ratio) | Peak Area Ratio (hydrophilic fractions:hydrophobic fractions) |
|---|---|---|---|
| Antibody A | Antibody C | | |
| 0.36 | 0.36 | 1:1 | 1.09:1 |
| 0.36 | 0.12 | 3:1 | 1.19:1 |
| 0.36 | 0.036 | 10:1 | 1.78:1 |
| 0.36 | 0.018 | 20:1 | 2.46:1 |
| 0.36 | 0.012 | 30:1 | 2.84:1 |

TABLE 2

| Antibody Concentration (μg/mL) | | Mixing Ratio by Weight (weight ratio) | Peak Area Ratio (hydrophilic fractions:hydrophobic fractions) |
|---|---|---|---|
| Antibody A | Antibody C | | |
| 0.36 | 0.12 | 3:1 | 1.19:1 |
| 0.12 | 0.12 | 1:1 | 1:1.23 |
| 0.036 | 0.12 | 0.3:1 | 1:1.70 |
| 0.012 | 0.12 | 0.1:1 | 1:1.88 |
| 0.006 | 0.12 | 0.05:1 | 1:2.07 |
| 0.0036 | 0.12 | 0.03:1 | 1:2.05 |

The invention claimed is:

1. An assay method for determining the presence of protein induced by vitamin K absence-II (PIVKA-II) in a sample, the method comprising
contacting the sample with (i) an anti-PIVKA-II antibody or antigen-binding fragment thereof which specifically binds to PIVKA-II or (ii) a mixture of at least one first anti-prothrombin antibody or antigen-binding fragment thereof and at least one second anti-prothrombin antibody or antigen-binding fragment thereof, wherein said first anti-prothrombin antibody or antigen-binding fragment thereof recognizes hydrophilic PIVKA-II molecules and wherein said second anti-prothrombin antibody or antigen-binding fragment thereof recognizes hydrophobic PIVKA-II molecules to allow specific binding between the PIVKA-II present in the sample and (i) the anti-PIVKA-II antibody or antigen-binding fragment thereof or (ii) the at least one first anti-prothrombin antibody or antigen-binding fragment thereof and/or the at least one second anti-prothrombin antibody or antigen-binding fragment thereof; and
determining the presence of the PIVKA-II in the sample by detecting a signal generated in connection with immune complexes formed with (i) using (ii) to detect the signal or with (ii) using (i) to detect the signal, as an indication of the presence of the PIVKA-II in the sample,
wherein the hydrophilic PIVKA-II molecules are hydrophilic components specifically obtained from a fraction of a PIVKA-II-containing eluate from a hydrophobic interaction chromatography, and
wherein the hydrophobic PIVKA-II molecules are hydrophobic components specifically obtained from the fraction of the PIVKA-II-containing eluate from the hydrophobic interaction chromatography.

2. The assay method according to claim 1, wherein the hydrophilic PIVKA-II molecules are PIVKA-II molecules contained in the hydrophobic interaction chromatography fraction of PIVKA-II-containing material eluted with ammonium sulfate at a concentration equal to or greater than a prescribed concentration which is set within a range of 270 mM to 370 mM, and the hydrophobic PIVKA II molecules are PIVKA-II molecules contained in the hydrophobic interaction chromatography fraction of PIVKA-II-containing material eluted with ammonium sulfate at a concentration less than the prescribed concentration, said fractions being obtained by fractionation of PIVKA-II-containing material with a linear concentration gradient of ammonium sulfate using a hydrophobic interaction chromatography column employing phenyl group as a functional group.

3. The assay method according to claim 2, wherein the prescribed concentration of ammonium sulfate is a concentration within the range of 290 mM to 350 mM.

4. The assay method according to claim 1, wherein the first anti-prothrombin antibody, the second anti-prothrombin antibody, and the anti-PIVKA-II antibody are monoclonal antibodies.

5. The assay method according to claim 1, wherein the immunoassay is performed by a sandwich method using said (ii) the at least one first anti-prothrombin antibody or antigen-binding fragment thereof and/or the at least one second anti-prothrombin antibody or antigen-binding fragment thereof as a labeled antibody and said (i) anti-PIVKA-II antibody or antigen-binding fragment thereof as an immobilized antibody.

6. The assay method according to claim 1, wherein said at least one first anti-prothrombin antibody or antigen-binding fragment thereof and said at least one second anti-prothrombin antibody or antigen-binding fragment thereof are contained in the mixture in a mixing ratio from 1:10 to 10:1.

7. The assay method according to claim 1, wherein the sample is serum or plasma.

8. A method for determining the presence of protein induced by vitamin K absence-II (PIVKA-II) in a sample, the method comprising:
contacting the sample with (i) an anti-PIVKA-II antibody or antigen-binding fragment thereof which specifically binds to PIVKA-II or (ii) a mixture of at least one first anti-prothrombin antibody or antigen-binding fragment thereof and at least one second anti-prothrombin antibody or antigen-binding fragment thereof to allow specific binding between the PIVKA-II present in the sample and said (i) or said (ii); and
determining the presence of the PIVKA-II in the sample by detecting a signal generated in connection with immune complexes formed with (i) using (ii) to detect the signal or with (ii) using (i) to detect the signal, as an indication of the presence of the PIVKA-II in the sample, wherein said first anti-prothrombin antibody is an antibody that reacts with hydrophobic interaction chromatography fractions of PIVKA-II-containing material eluted with ammonium sulfate at a concentration of equal to or greater than a prescribed concentration which is set within a range of 270 mM to 370 mM, and said second anti-prothrombin antibody is an antibody that reacts with hydrophobic interaction chromatography fractions of PIVKA-II-containing material eluted with ammonium sulfate at a concentration of less than the prescribed concentration, said fractions being obtained by fractionation of PIVKA-II-containing material with a linear concentration gradient of ammonium sulfate using a hydrophobic interaction chromatography column employing phenyl group as a functional group.

* * * * *

SEQUENCE LISTING

<160> NUMBER OF SEQ ID NOS: 2

<210> SEQ ID NO 1
<211> LENGTH: 622
<212> TYPE: PRT
<213> ORGANISM: Homo sapiens
<220> FEATURE:
<221> NAME/KEY: MOD_RES
<222> LOCATION: (49)..(49)
<223> OTHER INFORMATION: Gla or Glu
<220> FEATURE:
<221> NAME/KEY: MOD_RES
<222> LOCATION: (50)..(50)
<223> OTHER INFORMATION: Gla or Glu
<220> FEATURE:
<221> NAME/KEY: MOD_RES
<222> LOCATION: (57)..(57)
<223> OTHER INFORMATION: Gla or Glu
<220> FEATURE:
<221> NAME/KEY: MOD_RES
<222> LOCATION: (59)..(59)
<223> OTHER INFORMATION: Gla or Glu
<220> FEATURE:
<221> NAME/KEY: MOD_RES
<222> LOCATION: (62)..(62)
<223> OTHER INFORMATION: Gla or Glu
<220> FEATURE:
<221> NAME/KEY: MOD_RES
<222> LOCATION: (63)..(63)
<223> OTHER INFORMATION: Gla or Glu
<220> FEATURE:
<221> NAME/KEY: MOD_RES
<222> LOCATION: (68)..(68)
<223> OTHER INFORMATION: Gla or Glu
<220> FEATURE:
<221> NAME/KEY: MOD_RES
<222> LOCATION: (69)..(69)
<223> OTHER INFORMATION: Gla or Glu
<220> FEATURE:
<221> NAME/KEY: MOD_RES
<222> LOCATION: (72)..(72)
<223> OTHER INFORMATION: Gla or Glu
<220> FEATURE:
<221> NAME/KEY: MOD_RES
<222> LOCATION: (75)..(75)
<223> OTHER INFORMATION: Gla or Glu

<400> SEQUENCE: 1

```
Met Ala His Val Arg Gly Leu Gln Leu Pro Gly Cys Leu Ala Leu Ala
 1               5                  10                  15

Ala Leu Cys Ser Leu Val His Ser Gln His Val Phe Leu Ala Pro Gln
                20                  25                  30

Gln Ala Arg Ser Leu Leu Gln Arg Val Arg Arg Ala Asn Thr Phe Leu
            35                  40                  45

Xaa Xaa Val Arg Lys Gly Asn Leu Xaa Arg Xaa Cys Val Xaa Xaa Thr
        50                  55                  60
```

```
Cys Ser Tyr Xaa Xaa Ala Phe Xaa Ala Leu Xaa Ser Ser Thr Ala Thr
 65              70                  75                  80

Asp Val Phe Trp Ala Lys Tyr Thr Ala Cys Glu Thr Ala Arg Thr Pro
                 85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
            115                 120                 125

Cys Gln Leu Trp Arg Ser Arg Tyr Pro His Lys Pro Glu Ile Asn Ser
            130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
                180                 185                 190

Val Ala Met Thr Pro Arg Ser Glu Gly Ser Ser Val Asn Leu Ser Pro
            195                 200                 205

Pro Leu Glu Gln Cys Val Pro Asp Arg Gly Gln Gln Tyr Gln Gly Arg
210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
                260                 265                 270

Trp Cys Tyr Val Ala Gly Lys Pro Gly Asp Phe Gly Tyr Cys Asp Leu
            275                 280                 285

Asn Tyr Cys Glu Glu Ala Val Glu Glu Glu Thr Gly Asp Gly Leu Asp
            290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
                340                 345                 350

Arg Glu Leu Leu Glu Ser Tyr Ile Asp Gly Arg Ile Val Glu Gly Ser
                355                 360                 365

Asp Ala Glu Ile Gly Met Ser Pro Trp Gln Val Met Leu Phe Arg Lys
            370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
                420                 425                 430

Arg Tyr Glu Arg Asn Ile Glu Lys Ile Ser Met Leu Glu Lys Ile Tyr
            435                 440                 445

Ile His Pro Arg Tyr Asn Trp Arg Glu Asn Leu Asp Arg Asp Ile Ala
            450                 455                 460

Leu Met Lys Leu Lys Lys Pro Val Ala Phe Ser Asp Tyr Ile His Pro
465                 470                 475                 480
```

```
Val Cys Leu Pro Asp Arg Glu Thr Ala Ala Ser Leu Leu Gln Ala Gly
            485                 490                 495

Tyr Lys Gly Arg Val Thr Gly Trp Gly Asn Leu Lys Glu Thr Trp Thr
        500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
        530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
            565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
            595                 600                 605

Leu Lys Lys Trp Ile Gln Lys Val Ile Asp Gln Phe Gly Glu
        610                 615                 620

<210> SEQ ID NO 2
<211> LENGTH: 2018
<212> TYPE: DNA
<213> ORGANISM: Homo sapiens

<400> SEQUENCE: 2
gtcaggacag acaattcctc agtgacccag gagctgacac actatggcgc acgtccgagg      60
cttgcagctg cctggctgcc tggccctggc tgccctgtgt agccttgtgc acagccagca     120
tgtgttcctg gctcctcagc aagcacggtc gctgctccag cgggtccggc gagccaacac     180
cttcttggag gaggtgcgca agggcaacct ggagcgagag tgcgtggagg agacgtgcag     240
ctacgaggag gccttcgagg ctctggagtc ctccacggct acggatgtgt tctgggccaa     300
gtacacagct tgtgagacag cgaggacgcc tcgagataag cttgctgcat gtctggaagg     360
taactgtgct gagggtctgg gtacgaacta ccgagggcat gtgaacatca cccggtcagg     420
cattgagtgc cagctatgga ggagtcgcta cccacataag cctgaaatca actccactac     480
ccatcctggg gccgacctac aggagaattt ctgccgcaac cccgacagca gcaccacggg     540
accctggtgc tacactacag accccaccgt gaggaggcag aatgcagca tccctgtctg     600 tggccaggat caagtcactg tagcgatgac tccacgctcc gaaggctcca gtgtgaatct     660
gtcacctcca ttggagcagt gtgtccctga tcggggggcag cagtaccagg ggcgcctggc     720
ggtgaccaca catgggctcc cctgcctggc ctgggccagc gcacaggcca aggccctgag     780
caagcaccag gacttcaact cagctgtgca gctggtggaa aacttctgcc gcaacccaga     840 cgggatgag gagggcgtgt ggtgctatgt ggccgggaag cctggcgact ttgggtactg     900
cgacctcaac tattgtgagg aggccgtgga ggagagaca ggagatgggc tggatgagga     960
ctcagacagg gccatcgaag ggcgtaccgc caccagtgag taccagactt cttcaatcc    1020 gaggaccttt ggctcgggag aggcagactg tgggctgcga cctctgttcg agaagaagtc    1080
gctggaggac aaaaccgaaa gagagctcct ggaatcctac atcgacgggc gcattgtgga    1140
gggctcggat gcagagatcg gcatgtcacc ttggcaggtg atgctttcc ggaagagtcc    1200 ccaggagctg ctgtgtgggg ccagcctcat cagtgaccgc tgggtcctca ccgccgccca    1260
ctgcctcctg taccggccct gggacaagaa cttcaccgag aatgaccttc tggtgcgcat    1320
```

```
tggcaagcac tcccgcacca ggtacgagcg aaacattgaa aagatatcca tgttggaaaa    1380
gatctacatc caccccaggt acaactggcg ggagaacctg gaccgggaca ttgccctgat    1440
gaagctgaag aagcctgttg ccttcagtga ctacattcac cctgtgtgtc tgcccgacag    1500
ggagacggca gccagcttgc tccaggctgg atacaagggg cgggtgacag gctggggcaa    1560
cctgaaggag acgtggacag ccaacgttgg taaggggcag cccagtgtcc tgcaggtggt    1620
gaacctgccc attgtggagc ggccggtctg caaggactcc acccggatcc gcatcactga    1680
caacatgttc tgtgctggtt acaagcctga tgaagggaaa cgaggggatg cctgtgaagg    1740
tgacagtggg ggaccctttg tcatgaagag cccctttaac aaccgctggt atcaaatggg    1800
catcgtctca tggggtgaag gctgtgaccg ggatgggaaa tatggcttct acacacatgt    1860
gttccgcctg aagaagtgga tacagaaggt cattgatcag tttggagagt aggggggccac    1920 tcatattctg ggctcctgga accaatcccg tgaaagaatt atttttgtgt ttctaaaact    1980
atggttccca ataaaagtga ctctcagcga aaaaaaaa                            2018
```